(12) United States Patent
Grauert et al.

(10) Patent No.: US 6,245,777 B1
(45) Date of Patent: Jun. 12, 2001

(54) N-(5-PHENYL-TETRAHYDROFURANYL) METHYL- AND N-(6-PHENYL-TETRAHYDROPYRANYL)METHYL-SUBSTITUTED 1,2,3,4,5,6-HEXAHYDRO-2,6-METHANO-3-BENZAZOCIN-10-OLS

(75) Inventors: Matthias Grauert; Hans Briem; Matthias Hoffmann, all of Ingelheim; Adrian Carter, Bingen; Thomas Weiser, Nieder-Olm; Wolf-Dietrich Bechtel, Appenheim; Rainer Palluk, Bingen, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/510,555

(22) Filed: Feb. 22, 2000

Related U.S. Application Data

(60) Provisional application No. 60/134,658, filed on May 18, 1999.

(30) Foreign Application Priority Data

Feb. 23, 1999 (DE) ................................. 199 07 874

(51) Int. Cl.$^7$ ................... A61K 31/4748; C07D 405/06; C07D 221/26; A61P 25/00
(52) U.S. Cl. ............................. 514/295; 546/97
(58) Field of Search ................ 546/97; 514/295

(56) References Cited

U.S. PATENT DOCUMENTS 4,087,532 * 5/1978 Merz ..................................... 424/267

* cited by examiner

*Primary Examiner*—Evelyn Mei Huang
(74) *Attorney, Agent, or Firm*—Robert P. Raymond; Alan R. Stempel; Mary-Ellen M. Devlin

(57) ABSTRACT

The present invention relates to N-(5-phenyl-tetrahydrofuranyl)methyl- and N-(6-phenyl-tetrahydropyranyl)methyl-substituted 1,2,3,4,5,6-hexahydro-2,6-methano-3-benzazocin-10-ols of general formula 1, processes for preparing such compounds, pharmaceutical compositions containing such compounds and methods for using such compounds for the treatment of various diseases caused by a functional disorder resulting from overstimulation.

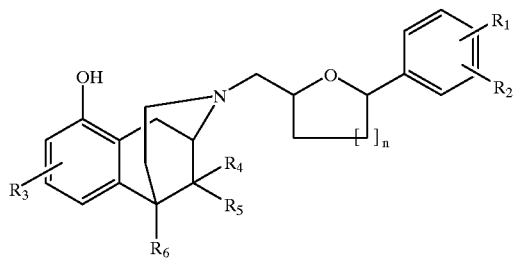

20 Claims, No Drawings

N-(5-PHENYL-TETRAHYDROFURANYL) METHYL- AND N-(6-PHENYL-TETRAHYDROPYRANYL)METHYL-SUBSTITUTED 1,2,3,4,5,6-HEXAHYDRO-2,6-METHANO-3-BENZAZOCIN-10-OLS

CROSS-REFERENCE TO RELATED APPLICATIONS

Benefit of U.S. Provisional Application Serial No. 60/134,658, filed on May 18, 1999, is hereby claimed.

FIELD OF THE INVENTION

The present invention relates to compounds, compositions and methods for the treatment of diseases caused by a functional disorder resulting from overstimulation. In particular, the present invention relates to N-(5-phenyl-tetrahydrofuranyl)methyl- and N-(6-phenyl-tetrahydropyranyl)methyl-substituted 1,2,3,4,5,6-hexahydro-2,6-methano-3-benzazocin-10-ols, processes for preparing such compounds, pharmaceutical compositions containing such compounds and methods for using these compounds for the treatment of diseases caused by a functional disorder resulting from overstimulation.

SUMMARY OF THE INVENTION

The present invention relates to N-(5-phenyl-tetrahydrofuranyl)methyl- and N-(6-phenyl-tetrahydropyranyl)methyl-substituted 1,2,3,4,5,6-hexahydro-2,6-methano-3-benzazocin-10-ols of general formula 1:

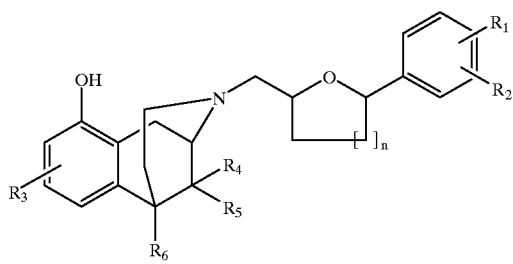

wherein $R_1$ is hydrogen, methyl or fluorine;

$R_2$ is hydrogen, methyl or fluorine;

n is an integer 1 or 2;

$R_3$ is hydrogen, fluorine, chlorine, bromine, methyl, ethyl, hydroxy, methoxy;

$R_4$ is hydrogen or methyl;

$R_5$ is hydrogen or methyl; and $R_6$ is hydrogen, methyl or ethyl.

The present invention is also directed to processes for preparing such compounds, pharmaceutical compositions containing such compounds and methods for using these compounds for the treatment of diseases caused by a functional disorder resulting from overstimulation.

DETAILED DESCRIPTION OF THE INVENTION

The preferred compounds of general formula 1 are those wherein:

$R_1$ is hydrogen or fluorine;

$R_2$ is hydrogen or fluorine;

n is 1;

$R_3$ is hydrogen, methyl;

$R_4$ is hydrogen or methyl;

$R_5$ is hydrogen or methyl; and $R_6$ is hydrogen, methyl or ethyl.

The invention relates to the compounds of formula 1, optionally in the form of the individual optical isomers, mixtures of the individual enantiomers, or racemates, and also in the form of the free bases or the corresponding acid addition salts thereof with pharmacologically acceptable acids such as, for example, acid addition salts with hydrohalic acids, e.g., hydrochloric or hydrobromic acid, or organic acids such as, e.g. oxalic, fumaric or diglycolic acid or methanesulphonic acid.

Biological Properties

The compounds claimed are blockers of the voltage-dependent sodium channel. These are compounds which displace batrachotoxin (BTX) with a high affinity ($K_i$<1000 nM) competitively or non-competitively from the binding site on the sodium channel. Such compounds exhibit "use-dependency" while the sodium channels are blocked, i.e. in order to bind the compounds at the sodium channel, the sodium channels first have to be activated. Maximum blockage of the sodium channels is only achieved after repeated stimulation of the sodium channels. Consequently, the compounds bind preferentially to sodium channels which are activated a number of times. As a result, the compounds are in a position to become effective particularly in those parts of the body which are pathologically overstimulated. The compounds of general formula 1 according to the invention can thus be used to treat diseases which are caused by a functional disorder resulting from overstimulation. These include diseases such as arrhythmias, spasms, cardiac and cerebral ischemias, pain and neurodegenerative diseases of various origins. These include, for example, epilepsy, hypoglycemia, hypoxia, anoxia, brain trauma, brain edema, cerebral stroke, perinatal asphyxia, degeneration of the cerebellum, amyotropic lateral sclerosis, Huntington's disease, Alzheimer's disease, Parkinson's disease, cyclophrenia, hypotonia, cardiac infarction, heart rhythm disorders, angina pectoris, chronic pain, neuropathic pain and local anaesthesia.

The blocking action on the sodium channel may be demonstrated by the test system which tests the BTX binding to the sodium channel [S. W. Postma & W. A. Catterall, Mol. Pharmacol 25, 219–227 (1984)] as well as by patch-clamp experiments which show that the compounds according to the invention block the electrically stimulated sodium channel in a "use-dependent" manner [W. A. Catterall, Trends Pharmacol. Sci., 8, 57–65 (1987)]. By a suitable choice of cell system (e.g. neuronal, cardiac, DRG cells) it is possible to test the effect of the substances on different subtypes of sodium channel.

The sodium channel blocking property of the compounds according to the invention can be demonstrated by the blocking of the veratridine-induced release of glutamate [S. Villanueva, P. Frenz, Y. Dragnic, F. Orrego, Brain Res. 461, 377–380 (1988)]. Veratridine is a toxin which opens the sodium channel permanently. This leads to an increased influx of sodium ions into the cell. By means of the cascade described above, this sodium influx leads to increased release of glutamate in the neuronal tissue. The compounds according to the invention antagonize this release of glutamate.

The anticonvulsant properties of the substances according to the invention were demonstrated by their protective effect against convulsions triggered by a maximum electric shock in mice [M. A. Rogawski & R. J. Porter, Pharmacol. Rev. 42, 223–286 (1990)].

Neuroprotective properties were demonstrated by a protective effect in a rat MCAO model [U. Pschorn & A. J. Carter, J. Stroke Cerebrovascular Diseases, 6, 93–99 (1996)] and a malonate-induced lesion model [M. F. Beal, Annals of Neurology, 38, 357–366 (1995) and J. B. Schulz, R. T. Matthews, D. R. Henshaw and M. F. Beal, Neuroscience, 71, 1043–1048 (1996)].

Analgesic effects can be investigated in models of diabetic neuropathy and in a ligature model [C. Courteix, M. Bardin, C. Chantelauze, J. Lavarenne, A. Eschalier, Pain 57, 153–160 (1994); C. Courteix, A. Eschalier, J. Lavarenne, Pain 53, 81–88 (1993); G. J. Bennett and Y.-K. Xie, Pain 33, 87–107 (1988)].

It has also been reported that sodium channel blockers can be used to treat cyclophrenia (manic depressive disorder) [J. R. Calabrese, C. Bowden, M. J. Woyshville; in: Psychopharmacology: The Fourth Generation of Progress (Eds.: D. E. Bloom and D. J. Kupfer) 1099–1111. New York: Raven Press Ltd.].

Preparation Methods

The compounds of formula 1 of the invention may be prepared by methods known per se from the prior art. One possible method of synthesis is shown in Diagram 1. The methods of synthesizing the nor-1,2,3,4,5,6-hexahydro-2,6-methano-3-benzazocin-10-ols 2 needed as starting compounds are described in published German applications 41 21 821, 195 28 472 and 197 40 110. The synthesis component 3 contains a leaving group X which is preferably iodine, bromine or a methanesulphonate group. The synthesis of the 5-phenyl-tetrahydrofuranyl)methyl-iodide is described in the literature [K. Miura, T. Hondo, S. Okajima, A. Hosomi, Tetrahedron Lett. 37 (1996) 487–490] for the racemate. The enantiomerically pure compounds may be prepared analogously, following this same procedure, if the corresponding chiral 5-hydroxy-5-phenyl-pentene is used as starting compound [cf. D. Seebach, R. E. Marti, T. Hintermann; Helv. Chim. Acta, 79 (1996) 1710–1740].—The corresponding bromides are prepared analogously if bromine is used instead of iodine.

The methanesulphonates of the 6-phenyl-tetrahydropyran-2-yl-methanols and 5-phenyl-tetrahydrofuran-2-yl-methanols may be prepared from the corresponding alcohols. The synthesis of 6-phenyl-tetrahydropyran-2-yl-methanol and 5-phenyl-tetrahydrofuran-2-yl-methanol is described in the literature [T. Mandai, M. Ueda, K. Kashiwagi, M. Kawada, J. Tsuji, Tetrahedron Lett., 34 (1993) 111–114; S. Inoki, T. Mukaiyama, Chemistry Lett. 1990, 67–70].

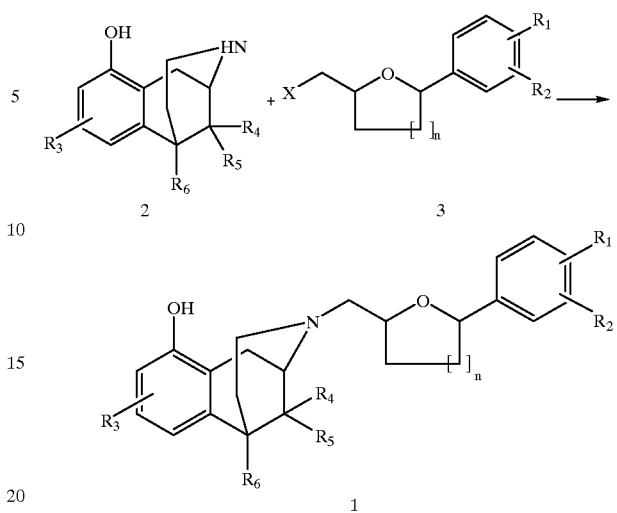

EXAMPLES

Example 1

(2R, 5S)- and (2S, 5S)-5-Phenyl-tetrahydrofuran-2-yl)methyl-bromide 1.6 g (10 mmol) of(5S)-5-hydroxy-5-phenyl-pentene are dissolved in 16 mL of dichloromethane and at 10 to 15° C. 1.6 g of bromine in 16 mL dichloromethane is added. The mixture is left to return to ambient temperature and 2 g of $Na_2CO_3$ (sodium carbonate) and 0.1 g of tetrabutyl ammoniumsulphate are added. After 1 hour (h) 20 mL of water are added and the mixture is stirred for another hour at ambient temperature. The organic phase is separated off, washed once with 20 mL of 2 N hydrochloric acid, dried and the solvent is eliminated in vacuo. The residue is chromatographed on 400 g of silica gel (cyclohexane/ethyl acetate: 95:5). 0.6 g (25% of theory) of (2S, 5S)-5-phenyl-tetrahydrofuran-2-yl)methyl-bromide and 0.7 g (29% of theory) of (2R, 5S)-5-phenyl-tetrahydrofuran-2-yl)methyl-bromide are obtained.

Example 2

(5-Phenyl-tetrahydrofuran-2-yl)methyl (2S, 5S)-methanesulphonate 580 mg (3.3 mmol) of (2S, 5S)-5-phenyl-tetrahydrofuran-2-yl)methanol are dissolved in 4 mL of pyridine and combined with 390 mg (3.4 mmol) of methanesulphonic acid chloride and stirred for 1 h at 0° C. and then for 8 h at ambient temperature. Next, 30 mL of water and 30 mL of 2 N hydrochloric acid are added. The mixture is extracted three times with 20 mL of diethylether, the ethereal phase is washed once with 50 mL of 10% $Na_2CO_3$ solution, dried, and the solvent is eliminated in vacuo. The residue is chromatographed over 20 g of silica gel (cyclohexane/ethyl acetate: 1:1). 450 mg (53% of theory) of the title compound are obtained as an oil.

Example 3

(2R,6S,2'R,5'S)-N-[(5'-phenyl-tetrahydrofuran-2'-yl) methyl]-1,2,3,4,5,6-hexahydro-6,11,11-trimethyl-2, 6-methano-3-benzazocin-10-ol-hydrochloride 0.5 g (2.15 mmol) of (2R,6S)-1,2,3,4,5,6-hexahydro-6,11, 11-trimethyl-2,6-methano-3-benzazocin-10-ol and 0.5 g (11 mmol) of (2R, 5S)-5-phenyl-tetrahydrofuran-2-yl)methyl-bromide are dissolved in 3 mL of 1,3-dimethyltetrahydropyrimidinone and 1 g of $K_2CO_3$ (potassium carbonate) is added. The mixture is heated for a period of 4 h to a temperature in the range from 80–90° C., left to cool, mixed with 100 mL of water and extracted twice with 100 mL of ethyl acetate (ethyl acetate). The combined organic extracts are washed three times with 100 mL of water, dried, and freed from solvent in vacuo. The residue is chromatographed over 30 g of silica gel (cyclohexane/ethyl acetate). The appropriate fractions are collected, the solvent is eliminated in vacuo, the residue is taken up in 50 mL of ether and the hydrochloride is precipitated with ethereal hydrochloric acid. In this way, 0.5 g (54% of theory) of the title compound is obtained in the form of crystals; melting point: 174° C., $[\alpha]_D^{20}=(-)$ 47.0° (c=1 in methanol).

The following is prepared analogously to Example 3:

(2R,6S,2'S,5'S)-N-[(5'-phenyl-tetrahydrofuran-2'-yl) methyl]-1,2,3,4,5,6-hexahydro-6,11,11-trimethyl-2,6-methano-3-benzazocin-10-ol-hydrochloride; melting point: 253° C., $[\alpha]_D^{20}=(-)$ 55,3° (c=1 in methanol).

(2R,6S,2'R,5'R)-N-[(5'-Phenyl-tetrahydrofuran-2'-yl) methyl]-1,2,3,4,5,6-hexahydro-6,11,11-trimethyl-2,6-methano-3-benzazocin-10-ol-hydrochloride; melting point: 157° C. and (2R,6S,2'S,5'R)-N-[(5'-Phenyl-tetrahydrofuran-2'-yl) methyl]-1,2,3,4,5,6-hexahydro-6,11,11-trimethyl-2,6-methano-3-benzazocin-10-ol-hydrochloride; melting point: 169° C.

(2R,5R)- and (2S,5R)-5-phenyl-tetrahydrofuran-2-yl) methyl-iodide are used as the mixture of isomers and the corresponding diastereomers are separated by chromatography.

Example 4

(2RS,6RS,2'S,5'S)-N-[(5'-Phenyl-tetrahydrofuran-2'-yl )methyl]-1,2,3,4,5,6-hexahydro-6,7-dimethyl-2,6-methano-3-benzazocin-10-ol-hydrochloride 440 mg (1.7 mmol) of (2RS,6RS)-1,2,3,4,5,6-hexahydro-6,7-dimethyl-2,6-methano-3-benzazocin-10-ol and 350 mg (1.6 mmol) of (5-phenyl-tetrahydrofuran-2-yl)methyl (2S, 5S)-methanesulphonate are dissolved in 3 mL of 1,3-dimethyltetrahydropyrimidinone and 1 g of $K_2CO_3$ is added. The mixture is heated to a temperature in the range from 80–90° C. over a period of 5 h, left to cool, 100 mL of water are added and the resulting mixture is extracted twice with 100 mL of ethyl acetate. The combined organic phases are washed three time with 100 mL of water, dried, and the solvent is evaporated down in vacuo. The residue is chromatographed over 30 g of silica gel (cyclohexane/ethyl acetate 3:1). The required fractions are collected, the solvent is eliminated in vacuo, the residue is taken up in 50 mL of ether and the hydrochloride is precipitated with ethereal hydrochloric acid. Yield: 370 mg (53%) of a 1:1 mixture of diastereomers, melting point: 155° C.

Pharmaceutical Preparations

The following are examples of pharmaceutical preparations containing the active substance of formula 1:

| Tablets: | |
| --- | --- |
| active substance of general formula 1 | 20 mg |
| magnesium stearate | 1 mg |
| lactose | 190 mg |
| Injectable solution | |
| active substance of general formula 1 | 0.3 mg |
| sodium chloride | 0.8 g |
| benzalkonium chloride | 0.01 mg |
| water for injections | ad 100 ml |

A solution similar to that shown above is suitable for nasal administration in a spray, or in conjunction with a device which produces an aerosol with a particle size preferably between 2 and 6 $\mu$M, for administration via the lungs.

Solution for Infusion

A 5% by weight xylitol or saline solution which contains the active substance in a concentration of 2 mg/ml, for example, is adjusted to a pH of about 4 using a sodium acetate buffer.

Infusible solutions of this kind may contain an active substance according to general formula 1 in an amount, based on the total mass of the pharmaceutical preparation, in the range from 0.001 to 5 wt. %, preferably in the range from 0.001 to 3 wt. % and most preferably in the range from 0.01 to 1 wt. %.

Capsules for Inhalation

The active substance according to general formula 1 in micronised form is packed into hard gelatine capsules (particle size substantially between 2 and 6 $\mu$M), optionally with the addition of micronised carrier substances, such as lactose. It can be inhaled using conventional equipment for powder inhalation. Between 0.2 and 20 mg of active substance and 0 to 40 mg of lactose are packed into each capsule.

| Aerosol for inhalation | |
| --- | --- |
| active substance of general formula 1 | 1 part |
| soya lecithin | 0.2 parts |
| propellent gas mixture | ad 100 |

The invention claimed is:

1. A compound of formula 1:

[Chemical structure 1 shown with OH, N, O, phenyl ring with R1, R2, and substituents R3, R4, R5, R6, with subscript n]

wherein $R_1$ is hydrogen, methyl or fluorine;

$R_2$ is hydrogen, methyl or fluorine;

n is 1 or 2;

$R_3$ is hydrogen, fluorine, chlorine, bromine, methyl, ethyl, hydroxy or methoxy;

$R_4$ is hydrogen or methyl;

$R_5$ is hydrogen or methyl; and $R_6$ is hydrogen, methyl or ethyl;

optionally in the form of an individual optical isomer, mixture of the individual enantiomers, a racemate, a free base or the corresponding acid addition salt with a pharmacologically acceptable acid.

2. A compound of formula 1 according to claim 1, wherein:

$R_1$ is hydrogen or fluorine;

$R_2$ is hydrogen or fluorine;

n is 1;

$R_3$ is hydrogen or methyl;

$R_4$ is hydrogen or methyl;

$R_5$ is hydrogen or methyl; and $R_6$ is hydrogen, methyl or ethyl.

3. A compound of formula 1 according to claim 2, selected from the group consisting of the following compounds:

(2R,6S,2'R,5'S)-N-[(5'-phenyl-tetrahydrofuran-2'-yl)methyl]-1,2,3,4,5,6-hexahydro-6,11,11-trimethyl-2,6-methano-3-benzazocin-10-ol-hydrochloride;

(2R,6S,2'S,5'S)-N-[(5'-phenyl-tetrahydrofuran-2'-yl)methyl]-1,2,3,4,5,6-hexahydro-6,11,11-trimethyl-2,6-methano-3-benzazocin-10-ol-hydrochloride;

(2R,6S,2'R,5'R)-N-[(5'-phenyl-tetrahydrofuran-2'-yl)methyl]-1,2,3,4,5,6-hexahydro-6,11,11-trimethyl-2,6-methano-3-benzazocin-10-ol-hydrochloride;

(2R,6S,2'S,5'R)-N-[(5'-phenyl-tetrahydrofuran-2'-yl)methyl]-1,2,3,4,5,6-hexahydro-6,11,11-trimethyl-2,6-methano-3-benzazocin-10-ol-hydrochloride; and (2RS,6RS,2'S,5'S)-N-[(5'-phenyl-tetrahydrofuran-2'-yl)methyl]-1,2,3,4,5,6-hexahydro-6,7-dimethyl-2,6-methano-3-benzazocin-10-ol-hydrochloride.

4. A process for preparing a compound of formula 1 according to claim 1, comprising reacting a norbenzomorphane compound of formula 2:

[Chemical structure 2 shown with OH, HN, and substituents R3, R4, R5, R6]

wherein $R_3$, $R_4$, $R_5$ and $R_6$ are defined as in claim 1, with a tetrahydrofuran or hexahydropyran compound of formula 3:

[Chemical structure 3 shown with X, O, phenyl ring with R1, R2, subscript n]

wherein $R_1$, $R_2$ and n are defined as in claim 1 and X represents a leaving group, and optionally purifying and isolating the end product.

5. A pharmaceutical composition comprising a compound according to claim 1, or the acid addition salt thereof, together with conventional excipients or carriers.

6. A pharmaceutical composition according to claim 5, wherein the composition is in the form of an infusible solution.

7. A pharmaceutical composition according to claim 6, wherein the content of the compound of formula 1 is within the range from 0.001 to 5 wt. %, based on the total mass of the pharmaceutical composition.

8. A pharmaceutical composition according to claim 7, wherein the content of the compound of formula 1 is within the range from 0.001 to 3 wt. %, based on the total mass of the pharmaceutical composition.

9. A pharmaceutical composition according to claim 8, wherein the content of the compound of formula 1 is within the range from 0.01 to 1 wt. %, based on the total mass of the pharmaceutical composition.

10. A pharmaceutical composition comprising a compound according to claim 2, or the acid addition salts thereof, together with conventional excipients or carriers.

11. A pharmaceutical composition according to claim 10, wherein the composition is in the form of an infusible solution.

12. A pharmaceutical composition according to claim 11, wherein the content of the compound of formula 1 is within the range from 0.001 to 5 wt. %, based on the total mass of the pharmaceutical composition.

13. A pharmaceutical composition according to claim 12, wherein the content of the compound of formula 1 is within the range from 0.001 to 3 wt. %, based on the total mass of the pharmaceutical composition.

14. A pharmaceutical composition according to claim 13, wherein the content of the compound of formula 1 is within the range from 0.01 to 1 wt. %, based on the total mass of the pharmaceutical composition.

15. A method of treating a functional disorder caused by overstimulation of voltage-dependent sodium channel comprising administering a compound according to claim 1, or a pharmaceutical composition comprising said compound, in an amount effective to block the voltage-dependent sodium channel to a host in need of such treatment.

16. A method according to claim 15, wherein the functional disorder is selected from the group consisting of arrhythmias, spasms, cardiac and cerebral ischemia, pain and neurodegenerative disorders.

17. A method according to claim 16, wherein the functional disorder is selected from the group consisting of epilepsy, hypoglycemia, hypoxia, anoxia, brain trauma, brain edema, cerebral stroke, perinatal asphyxia, degeneration of the cerebellum, amyotropic lateral sclerosis, Huntington's disease, Parkinson's disease, cyclophrenia, hypotonia, cardiac infarct, heart rhythm disorders, angina pectoris, chronic pain, and neuropathic pain.

18. A method of treating a functional disorder caused by overstimulation of voltage-dependent sodium channel comprising administering a compound according to claim 2, or a pharmaceutical composition comprising said compound in an amount effective to block the voltage-dependent sodium channel to a host in need of such treatment.

19. A method according to claim 18, wherein the functional disorder is selected from the group consisting of arrhythmias, spasms, cardiac and cerebral ischemia, pain and neurodegenerative disorders.

20. A method according to claim 19, wherein the functional disorder is selected from the group consisting of epilepsy, hypoglycemia, hypoxia, anoxia, brain trauma, brain edema, cerebral stroke, perinatal asphyxia, degeneration of the cerebellum, amyotropic lateral sclerosis, Huntington's disease, Parkinson's disease, cyclophrenia, hypotonia, cardiac infarct, heart rhythm disorders, angina pectoris, chronic pain, and neuropathic pain.

* * * * *